(12) United States Patent
Zwart et al.

(10) Patent No.: US 8,283,494 B2
(45) Date of Patent: Oct. 9, 2012

(54) PROCESS FOR THE PREPARATION OF UREA

(75) Inventors: Stephen Rudolf Alexander Zwart, Sittard (NL); Johannes Henricus Mennen, Meijel (NL)

(73) Assignee: Stamicarbon B.V., Sittard (NL)

( * ) Notice: Subject to any disclaimer, the term of this patent is extended or adjusted under 35 U.S.C. 154(b) by 215 days.

(21) Appl. No.: 12/518,118

(22) PCT Filed: Dec. 3, 2007

(86) PCT No.: PCT/EP2007/063124
§ 371 (c)(1),
(2), (4) Date: Feb. 16, 2010

(87) PCT Pub. No.: WO2008/068210
PCT Pub. Date: Jun. 12, 2008

(65) Prior Publication Data
US 2010/0168473 A1    Jul. 1, 2010

(30) Foreign Application Priority Data
Dec. 8, 2006    (EP) ..................................... 06025387

(51) Int. Cl.
*C07C 273/04*    (2006.01)
(52) U.S. Cl. ................. 564/67; 564/70; 564/71; 564/72
(58) Field of Classification Search .................... 564/67, 564/70, 71, 72
See application file for complete search history.

(56) References Cited

U.S. PATENT DOCUMENTS

| 6,093,850 A | 7/2000 | Kojima et al. |
| 6,284,922 B1 | 9/2001 | Pagani et al. |
| 2008/0219900 A1 | 9/2008 | Romiti et al. |

FOREIGN PATENT DOCUMENTS

| EP | 0 329 215 | 8/1989 |
| WO | WO 2006/061083 | 6/2006 |

OTHER PUBLICATIONS

International Search Report for PCT/EP2007/063124, mailed Mar. 5, 2008.

*Primary Examiner* — Peter G O Sullivan
(74) *Attorney, Agent, or Firm* — Nixon & Vanderhye P.C.

(57) ABSTRACT

Process for the preparation of urea from ammonia and carbon dioxide in a urea production process comprising, in a high-pressure synthesis section: a. a reactor, wherein ammonia and carbon dioxide react to form a urea-comprising synthesis solution; b. a stripper, wherein the urea-comprising synthesis solution is heated and stripped, optionally in counter-current with a stripping agent; c. a submerged condenser, wherein the gas leaving the top of the stripper is, at least partially, condensed to form a condensate solution and d. an ejector, in the line connecting the submerged condenser and the reactor, supporting the transport of the condensate solution from the submerged condenser to the reactor, wherein a gas stream leaving the top of the submerged condenser is controlled by one or more controlling elements.

10 Claims, 4 Drawing Sheets

PROCESS FOR THE PREPARATION OF UREA

This application is the U.S. national phase of International Application No. PCT/EP2007/063124 filed 3 Dec. 2007, which designated the U.S. and claims priority to Europe Application No. 06025387.9 filed 8 Dec. 2006, the entire contents of each of which are hereby incorporated by reference.

FIELD

The invention relates to a process for the preparation of urea from ammonia and carbon dioxide in a urea production process comprising, in a high-pressure synthesis section
  a. a reactor, wherein ammonia and carbon dioxide react to form a urea-comprising synthesis solution,
  b. a stripper, wherein the urea-comprising synthesis solution is heated and stripped optionally in counter-current with a stripping agent,
  c. a submerged condenser, wherein the gas leaving the top of the stripper is, at least partially, condensed to form a condensate solution and
  d. an ejector, in the line connecting the submerged condenser and the reactor, supporting the transport of the condensate solution from the submerged condenser to the reactor.

BACKGROUND AND SUMMARY

Such a process for the preparation of urea is, for instance, described in EP 0834501 A2.

This patent publication describes the use of an ejector in the line connecting a submerged condenser and a reactor to be able to place the reactor and other equipment in a process for the preparation of urea on ground level. Liquid ammonia is used as the motive agent for the ejector.

The problem with the process as described in the prior art is, however, that when there is a low availability of liquid ammonia there is no proper motive agent for the ejector available to convey the condensate solution from the submerged condenser to the reactor. Low availability of liquid ammonia occurs, for instance, during a start-up of the process and when the process can not run at its full capacity for other reasons. To let the process run under these circumstances in the process according to the prior art liquid ammonia needs to be dosed as a motive agent to the ejector to keep the process running. Consequently, when all the liquid ammonia is used as motive agent, no ammonia is available anymore to adjust the ammonia to carbon dioxide molar ratio (N/C ratio) elsewhere in the high-pressure synthesis section of the urea production process. Adjustment of the N/C ratio is needed to prevent that an excess of non-condensed gases from the submerged condenser causes process upsets in parts of the high-pressure synthesis section downstream of the submerged condenser. The process upsets result, for instance, in a too high N/C ratio in the urea solution that leaves the reactor and thus result in a low amount of ammonia that is converted to urea.

The invention is characterized in that a gas stream leaving the top of the submerged condenser is controlled by one or more controlling elements.

It has surprisingly been found that by controlling the gas stream leaving the top of the condenser by one or more controlling elements the pressure drop over the ejector decreases resulting in the need of less motive agent for the ejector. In this way the amount of liquid ammonia needed as motive agent for the ejector is minimized and thus liquid ammonia can also be used for controlling the N/C ratio elsewhere in the high-pressure synthesis section. In this way it is possible to run the reactor at a lower capacity than its full capacity at optimal synthesis conditions and thus having a good ammonia conversion to urea.

DETAILED DESCRIPTION

Figure 1:
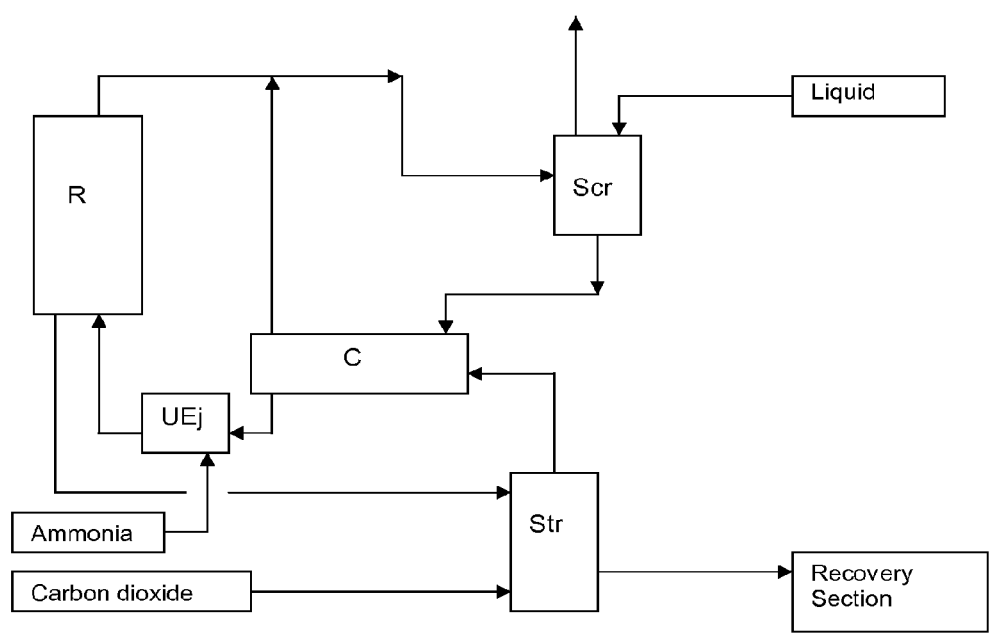
FIG. 1 is a schematic representation of a high-pressure synthesis section of the process employed in Comparative Experiment A below.

The invention is directed to a process for the preparation of urea from ammonia and carbon dioxide in a urea production process. A urea production process comprises normally a high-pressure synthesis section and one or more recovery sections that operate at lower pressure. In the high-pressure synthesis section the pressure is substantially equal to the urea synthesis pressure in the reactor, which is the pressure at which urea formation takes place in the reactor and is usually a pressure between 11-40 MPa, preferably 12.5-19 MPa. The pressure in the stripper, the submerged condenser and the ejector is substantially equal to the pressure in the reactor. Substantially equal means that the pressure in the stripper and/or submerged condenser is less than 1.5 MPa higher or lower than in the reactor.

In the recovery sections ammonia and carbon dioxide that did not react to form urea are further recovered from the urea-comprising product stream, produced in the high-pressure synthesis section, in order to be recycled to the high-pressure section. In the recovery sections the pressure is lower than in the high-pressure section. Recovery sections can operate at medium pressure and/or at low pressure. When more than one recovery section is present at least one of the recovery sections is operated at low pressure.

Medium pressure is a pressure between 1.0 and 8.0 MPa, preferably between 1.2 and 3.0 MPa.

Low pressure is a pressure between 0.2 and 0.8 MPa, preferably between 0.3 and 0.5 MPa.

A high-pressure synthesis section comprises:
  a. a reactor, wherein ammonia and carbon dioxide react to form a urea-comprising synthesis solution,
  b. a stripper, wherein the urea-comprising synthesis solution is heated and stripped optionally in counter-current with a stripping gas,
  c. a submerged condenser, wherein the gas leaving the top of the stripper is, at least partially, condensed to form a condensate solution and
  d. an ejector, in the line connecting the submerged condenser and the reactor, supporting the transport of the condensate solution from the submerged condenser to the reactor.

Urea can be prepared by introducing excess ammonia together with carbon dioxide into a reactor at a high pressure and elevated temperature (for example 160-250° C.), which first results in the formation of ammonium carbamate according to the reaction:

$$2NH_3 + CO_2 \rightarrow H_2N\text{---}CO\text{---}ONH_4$$

Dehydration of the ammonium carbamate formed then results in the formation of urea according to the equilibrium reaction:

$$H_2N\text{---}CO\text{---}ONH_4 \leftrightarrow H_2N\text{---}CO\text{---}NH_2 + H_2O$$

The theoretical maximum conversion of ammonia and carbon dioxide into urea is determined by the thermodynamic position of the equilibrium and depends on, for example, the N/C ratio, the water to carbon dioxide molar ratio (H/C ratio) and the temperature.

The reactor may consist of separate zones for the formation of ammonium carbamate and urea. These zones may be combined in one apparatus. The urea synthesis may be carried out in one or two reactors. When use is made of two reactors, the first reactor may for example be operated using virtually fresh ammonia and carbon dioxide and the second one using ammonia and carbon dioxide that are obtained entirely or partly elsewhere in the urea production process and that are recycled to the reactor.

During the conversion of ammonia and carbon dioxide into urea in the reactor a urea-comprising synthesis solution is obtained as a reaction product which consists essentially of urea, water, ammonium carbamate, unbound carbon dioxide and unbound ammonia. The urea-comprising synthesis solution is sent from the reactor to the stripper, where the solution is stripped by heat, optionally in countercurrent with ammonia or carbon dioxide, used as the stripping agent.

In the submerged condenser the gas released from the top of the stripper is, at least partially, condensed to form a condensate solution. The submerged condenser is, for instance, described in EP-A-0155735 or EP-A-0834501. A submerged condenser can also be a falling-film condenser transformed into a submerged condenser as described in EP-A-1036787. The submerged condenser can be placed horizontally, vertically or at any angle between a horizontal and a vertical position.

The condensate solution obtained in the submerged condenser is returned to the reactor, via the ejector that is placed in the line connecting the submerged condenser and the reactor. The ejector can be driven by liquid ammonia. The ejector supports the transport of the condensate solution from the condenser to the reactor. The condensate solution comprises urea. Preferably, the condensate solution comprises 5-30 wt % urea.

The gas stream leaving the top of the condenser is controlled by one or more controlling elements. One skilled in the art also has at their disposal an arsenal of controlling elements that may be used in the present invention. Suitable controlling elements include control valves (also known as regulating valves), shut-off valves and limited or calibrated restriction orifices in the conduit transporting the gas stream leaving the top of the submerged condenser. If a plurality of controlling elements is used, these may be of the same type but also may be of a different type. It is possible, for instance, to install restriction orifices suitably sized to ensure a pressure drop. In place thereof it is also possible to install in the conduit, transporting the gas stream leaving the top of the submerged condenser, adjustable pressure regulating valves that impart maximum flexibility to the process, in which case the investment costs will in principle be higher.

Preferably, as the controlling element a valve is used because these are easily adjustable.

The gas stream leaving the top of the reactor is a gas mixture of unconverted ammonia and carbon dioxide together with inert gases. Before the gas is vented to the atmosphere, ammonia and carbon dioxide may be removed from it by absorption in a liquid stream in the high-pressure scrubber. The high-pressure synthesis section in the process for the preparation of urea can also comprise such a scrubber, wherein the gas stream leaving the top of the submerged condenser is at least partially absorbed in a liquid stream.

Apart from the gas stream leaving the top of the submerged condenser also a gas stream leaving the top of the reactor can, at least partially, be absorbed in the liquid stream in the high-pressure scrubber. The liquid stream is originating from one of the recovery sections and can comprise ammonia, carbon dioxide, water, ammonium carbamate and traces of urea. The ammonia and carbon dioxide, dissolved in the liquid stream, are normally returned to the reactor directly or via the submerged condenser.

The scrubber can be placed in a higher position in the urea production process than the submerged condenser. The position of the scrubber in the urea production process can be determined freely when a second ejector is used for the transport of the liquid stream leaving the scrubber to the reactor and/or the submerged condenser. The second ejector can be driven by liquid ammonia or by a carbamate solution that is originating from one of the recovery sections.

When the scrubber is in a higher position than the submerged condenser and when the height difference between the scrubber and the submerged condenser is large enough the second ejector is not needed and the liquid stream leaving the scrubber is transported to the submerged condenser by gravity.

The invention is also directed to a plant for the preparation of urea from ammonia and carbon dioxide comprising, in a high-pressure synthesis section, a reactor, a stripper, a submerged condenser and an ejector, in the line connecting the submerged condenser and the reactor, wherein a conduit is present that is connected to the top of the submerged condenser and that comprises one or more controlling elements.

The plant according to the invention can also comprise a scrubber and a conduit connecting the scrubber and the top of the submerged condenser and further the high-pressure synthesis section can also contain a conduit connecting the scrubber and the top of the reactor.

The position of the scrubber in the urea production process can be determined freely when a conduit leaving the scrubber is connected to a second ejector that is also connected, via another conduit, to the reactor.

The invention is further directed to a process for the optimization of a plant for the preparation of urea from ammonia and carbon dioxide comprising, in a high-pressure synthesis section, a reactor, a stripper, a submerged condenser and an ejector, in the line connecting the submerged condenser and the reactor, wherein in a conduit, connected to the top of the submerged condenser, one or more controlling elements are placed.

The invention will hereafter be explained in more detail in the examples without being limited thereto.

EXAMPLES

Comparative Experiment A

Comparative experiment A refers to a standard $CO_2$ stripping process for the preparation of urea. The high-pressure synthesis section of the process is represented by FIG. 1.

The urea-comprising synthesis solution leaving the reactor (R) was conveyed to the stripper (Str). In the stripper a large part of the non-converted ammonia and carbon dioxide was removed from the urea-comprising synthesis solution by using heat and fresh carbon dioxide as the stripping agent. The urea-comprising solution leaving the stripper was sent to a recovery section operated at a lower pressure than the synthesis pressure. The gas leaving the top of the stripper was sent to the submerged condenser (C) wherein ammonia and carbon dioxide were condensed. Because of the retention time in the submerged condenser, the conversion of ammonia and carbon dioxide into urea took partly place in the submerged condenser. The condensate solution, comprising urea, water and carbamate, was conveyed to the reactor by a high-pressure ejector (UEj) driven by liquid ammonia.

The gas stream leaving the top of the submerged condenser was released to a high-pressure scrubber (Scr).

The gaseous non-converted ammonia and carbon dioxide, containing some inert gases, leaving the top of the reactor were also sent to the high-pressure scrubber (Scr). In this scrubber the main part of the ammonia and carbon dioxide was condensed and absorbed in a liquid solution originating from the recovery section. The inert gases, containing now only small amounts of ammonia and carbon dioxide, were sent directly into the atmosphere or were sent to an absorber in order to minimize gaseous ammonia emissions.

The formed condensate solution in the high-pressure scrubber was conveyed to the submerged condenser by gravity.

Example I

Figure 2:
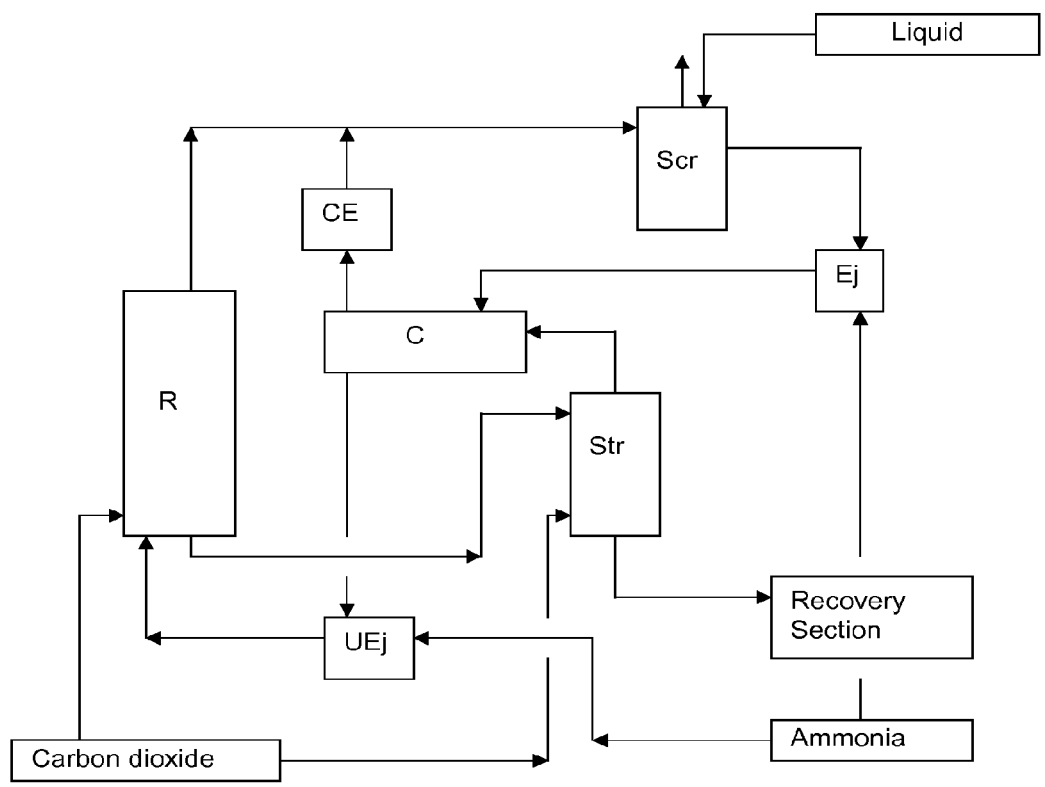
FIG. 2 is a schematic representation of a high-pressure synthesis section of a process in accordance with an embodiment of the invention employed in Example I below.

A process for the preparation of urea according to the invention is represented by FIG. 2. Only the high-pressure synthesis section of the process is represented by FIG. 2.

Similar to Comparative Experiment A, a urea-comprising synthesis solution from the high-pressure reactor (R) was sent to the stripper (Str). The reactor was located at ground level. In the stripper, the non-converted ammonia and carbon dioxide were separated from the urea-comprising synthesis solution by using heat and fresh carbon dioxide as stripping agent. The gas, leaving the top of the stripper, was sent to the submerged condenser (C). In the submerged condenser (C) the ammonia and carbon dioxide were condensed and urea formation took partly place. The condensate solution, comprising urea, water and carbamate, was conveyed to the reactor by a high-pressure ejector (UEj) driven by liquid ammonia.

The gas stream leaving the top of the submerged condenser was released via a control element (CE) to a high-pressure scrubber (Scr). In the scrubber (Scr) the main part of the gas, containing ammonia and carbon dioxide, was condensed together with the vapour leaving the top of the reactor by using a liquid from the downstream recovery section as absorbent and cooling water as cooling agent. The liquid stream that left the high-pressure scrubber was sent to the submerged condenser. The conveyance of the liquid stream to the condenser was done by using a second ejector (Ej) driven by liquid ammonia.

According to Example I the amount of ammonia that, according to Comparative Experiment A was used as motive fluid for one ejector, is now used as the motive fluid for two ejectors.

Example II

Figure 3:
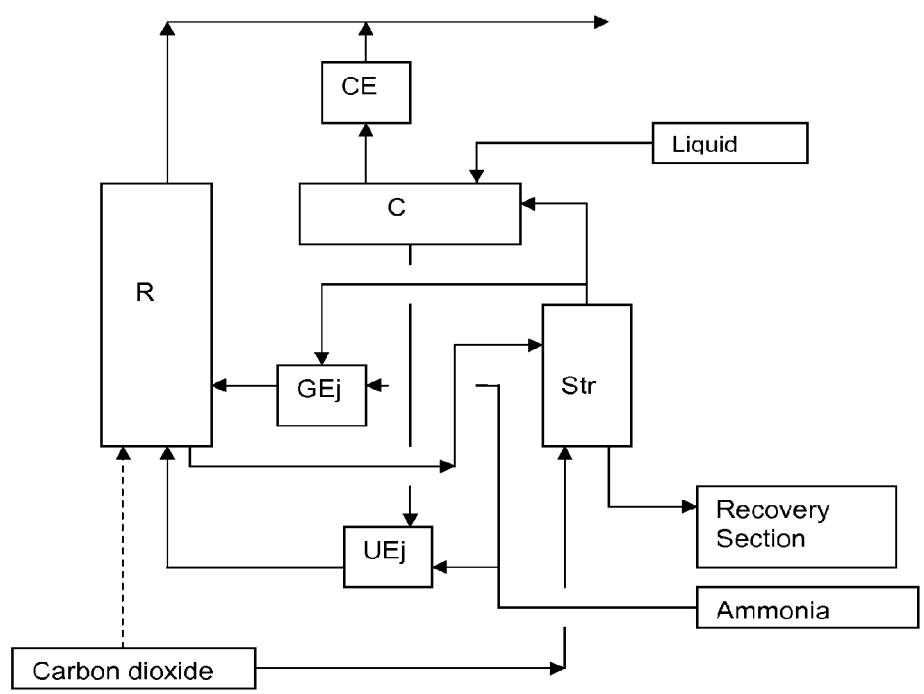
FIG. 3 is a schematic representation of a high-pressure synthesis section of a process in accordance with another embodiment of the invention employed in Example II below.

A process for the preparation of urea according to the invention is represented by FIG. 3. Only the high-pressure synthesis section of the process is represented by FIG. 3.

A urea-comprising synthesis solution from the reactor (R) was sent to the stripper (Str). The reactor was located at ground level. In the stripper, the non-converted ammonia and carbon dioxide were separated from the urea-comprising synthesis solution by using heat and fresh carbon dioxide as stripping agent. The gas, leaving the top of the stripper, was mainly sent to the submerged condenser (C) in which the ammonia and carbon dioxide were condensed and urea conversion took partly place. A part of the gas, leaving the top of the stripper, was sent to the reactor in order to reduce the required amount of fresh carbon dioxide needed for the heat input for the endothermic urea conversion reaction in this reactor. To overcome the pressure drop, an ejector (GEj) driven by heated liquid ammonia was used.

The condensate solution leaving the submerged condenser, containing urea, water and carbamate, was conveyed to the reactor by an ejector (UEj) driven by liquid ammonia. The gas leaving the submerged condenser was released via a control element (CE) and was, together with the gas leaving the top of the reactor, sent to the downstream processing where the ammonia and carbon dioxide were separated from the inert gas.

According to Example II the amount of ammonia that, according to Comparative Experiment A was used as motive fluid for one ejector, is now used as the motive fluid for two ejectors.

Example III

Figure 4:
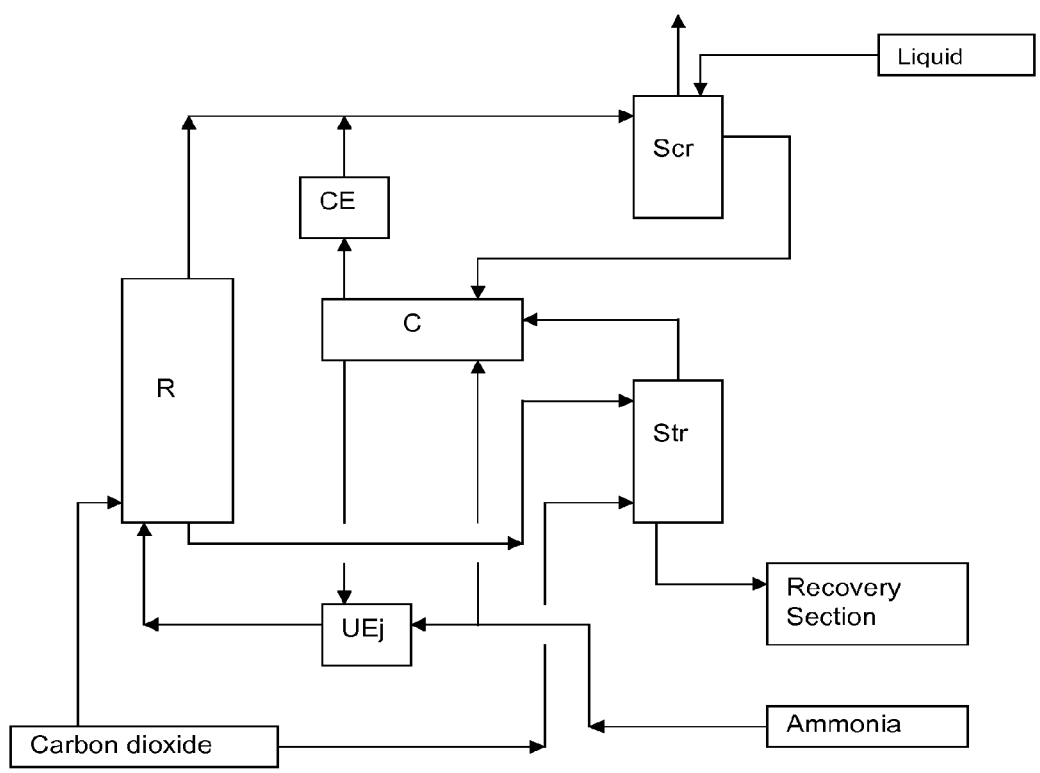
FIG. 4 is a schematic representation of a high-pressure synthesis section of a process in accordance with another embodiment of the invention employed in Example III below.

A process for the preparation of urea according to the invention is represented by FIG. 4. Only the high-pressure synthesis section of the process is represented by FIG. 4.

Similar to Comparative Experiment A, a urea-comprising synthesis solution from the high-pressure reactor (R) was sent to the stripper (Str). The reactor was located at ground level. In the stripper, the non-converted ammonia and carbon dioxide were separated from the urea-comprising synthesis solution by using heat and fresh carbon dioxide as stripping agent. The gas, leaving the top of the stripper, was sent to the submerged condenser (C). To the submerged condenser fresh liquid ammonia was fed. In the submerged condenser (C) the ammonia and carbon dioxide were condensed and urea formation took partly place. The condensate solution, comprising urea, water and carbamate, was conveyed to the reactor by a high-pressure ejector (UEj) driven by liquid ammonia.

The gas stream leaving the top of the submerged condenser was released via a control element (CE) to a high-pressure scrubber (Scr). In the scrubber (Scr) the main part of the gas, containing ammonia and carbon dioxide, was condensed together with the vapour leaving the top of the reactor by using a liquid from the downstream recovery section as absorbent and cooling water as cooling agent. The liquid stream that left the high-pressure scrubber was sent to the submerged condenser.

According to Example III the amount of ammonia that, according to Comparative Experiment A was used as motive fluid for one ejector, is now partly used as a motive fluid for an ejector and partly fed directly to the submerged condenser.

The invention claimed is:

1. A process for the preparation of urea from ammonia and carbon dioxide in a high pressure synthesis section of a urea production process comprising,
   (a) reacting ammonia and carbon dioxide in a reactor to form a urea-comprising synthesis solution,
   (b) heating and stripping the urea-comprising synthesis solution in a stripper, optionally in counter-current with a stripping agent, (c) at least partially condensing the gas leaving the top of the stripper in a submerged condenser to form a condensate solution, (d) supporting the transport of the condensate solution from the submerged condenser to the reactor with an ejector positioned in a line connecting the submerged condenser and the reactor, and (e) controlling a gas stream leaving a top of the submerged condenser by one or more controlling elements.

2. The process according to claim 1, wherein the condensate solution from the submerged condenser comprises 5-30 wt % urea.

3. The process according to claim 1, wherein the high-pressure synthesis section of the urea production process also comprises a scrubber, and wherein the process further comprises at least partially absorbing the gas stream leaving the top of the submerged condenser in a liquid stream of the scrubber.

4. The process according to claim 3, which further comprises at least partially absorbing a gas stream leaving the top of the reactor in the liquid stream of the scrubber.

5. The process according to claim 3, further comprising sending the liquid stream leaving the scrubber to the reactor and/or the submerged condenser using a second ejector.

6. A plant for the preparation of urea from ammonia and carbon dioxide comprising, in a high-pressure synthesis section, a reactor, a stripper, a submerged condenser, an ejector positioned in a line connecting the submerged condenser and the reactor, and a conduit connected to a top of the submerged condenser, wherein the conduit comprises one or more controlling elements.

7. The plant according to claim 6, wherein the high-pressure synthesis section also comprises a scrubber and a conduit connecting the top of the submerged condenser and the scrubber.

8. The plant according to claim 7, wherein the high-pressure synthesis section also comprises a conduit connecting the top of the reactor and the scrubber.

9. The plant according to claim 7, further comprising a second ejector, a first conduit leaving the scrubber which is connected to the second ejector, and a second conduit which connects the second ejector to the submerged condenser.

10. A process for the optimization of a plant for the preparation of urea from ammonia and carbon dioxide comprising, in a high-pressure synthesis section, a reactor, a stripper, a submerged condenser and an ejector, in the line connecting the submerged condenser and the reactor, the method comprising providing one or more controlling elements in a conduit which is connected to a top of the submerged condenser.

* * * * *